US012779452B2

(12) United States Patent
Rodriguez

(10) Patent No.: US 12,779,452 B2
(45) Date of Patent: Nov. 3, 2026

(54) APPARATUS FOR MICROORGANISM ISOLATION, CHARACTERIZATION, AND IDENTIFICATION, AND METHODS OF USE

(71) Applicant: ECOBIOME HOLDINGS LLC, The Woodlands, TX (US)

(72) Inventor: Marc Rodriguez, The Woodlands, TX (US)

(73) Assignee: EcoBiome Holdings LLC, The Woodlands, TX (US)

( * ) Notice: Subject to any disclaimer, the term of this patent is extended or adjusted under 35 U.S.C. 154(b) by 199 days.

(21) Appl. No.: 18/540,243

(22) Filed: Dec. 14, 2023

(65) Prior Publication Data

US 2024/0109062 A1 Apr. 4, 2024

Related U.S. Application Data

(60) Continuation of application No. 17/895,616, filed on Aug. 25, 2022, now Pat. No. 11,845,077, which is a division of application No. 16/258,112, filed on Jan. 25, 2019, now abandoned.

(60) Provisional application No. 62/622,493, filed on Jan. 26, 2018.

(51) Int. Cl.

| | |
|---|---|
| ***B01L 3/00*** | (2006.01) |
| ***C12M 1/00*** | (2006.01) |
| ***C12M 1/24*** | (2006.01) |
| ***C12N 5/00*** | (2006.01) |

(52) U.S. Cl.

CPC ............... *B01L 3/50* (2013.01); *C12M 23/08* (2013.01); *C12M 23/22* (2013.01); *C12M 23/38* (2013.01); *C12N 5/0018* (2013.01); *B01L 2300/042* (2013.01); *B01L 2300/0832* (2013.01); *C12N 2500/32* (2013.01); *C12N 2500/38* (2013.01)

(58) Field of Classification Search

CPC .................................. C12M 23/08; B01L 3/12

See application file for complete search history.

(56) References Cited

U.S. PATENT DOCUMENTS

| | | | |
|---|---|---|---|
| 3,275,528 | A | 9/1966 | Ainis |
| 3,793,154 | A | 2/1974 | Efthymion |
| 4,579,631 | A | 4/1986 | Ishikawa |
| 4,596,779 | A | 6/1986 | Ono |
| 4,683,207 | A | 7/1987 | Waarvik |
| 7,381,559 | B2 | 6/2008 | Ellis |

(Continued)

FOREIGN PATENT DOCUMENTS

WO WO2017/210236 A1 12/2017

OTHER PUBLICATIONS

"Corning® 125 mL Disposable Spinner Flask with 70 mm Top Cap and 2 Angled Sidearms, Sterile", downloaded from the Internet on Feb. 5, 2023 at url: https://ecatalog.corning.com/life-sciences/b2c/US/en/Bioprocess-and-Scale-up/Disposable-Spinner-Flasks/Corning%C2%AE-Disposable-Spinner-Flasks/p/3152, Corning Inc.

(Continued)

*Primary Examiner* — Jonathan M Hurst

(74) *Attorney, Agent, or Firm* — Jeffren L. Wendt; Stibbs & Co., P.C.

(57) ABSTRACT

The present disclosure relates generally to an apparatus and methods for microorganism isolation, characterization and identification based on oxygen, pressure, culture media gradients and metabolites. In each embodiment, the apparatus of the disclosure is particularly useful for the purpose of novel isolation of never before cultured species of microorganisms and their by-products.

9 Claims, 2 Drawing Sheets

(56) References Cited

U.S. PATENT DOCUMENTS

| | | | |
|---|---|---|---|
| 8,057,092 | B2 | 11/2011 | Ryan |
| 10,501,720 | B2 | 12/2019 | Shor |
| 10,920,185 | B2 | 2/2021 | Scibek et al. |
| 2009/0311776 | A1 | 12/2009 | Kelly |

OTHER PUBLICATIONS

Orizondo et al., "Effects of Emulsion Composition on Pulmonary Tobramycin Delivery During Antibacterial Perfluorocarbon Ventilation", 2016, J. of Aerosol Med. and Pulm. Drug Del. 29(3), pp. 251-259.
Rodriguez, USPTO Form PTO/SB/08A from Information Disclosure Statement filed in U.S. Appl. No. 16/258,112, filed Jan. 25, 2019.
USPTO, Office Action mailed Mar. 1, 2021 in U.S. Appl. No. 16/258,112, filed Jan. 25, 2019, 10 pages.
Rodriguez, Response filed Jun. 1, 2021, to USPTO Office Action mailed Mar. 1, 2021 in U.S. Appl. No. 16/258,112, 10 pages.
USPTO, Office Action mailed Jul. 6, 2021 in U.S. Appl. No. 16/258,112, filed Jan. 25, 2019, 13 pages.
Rodriguez, Response filed Oct. 5, 2021 with RCE, to USPTO Office Action mailed Jul. 6, 2021 in U.S. Appl. No. 16/258,112, 13 pages.
USPTO, Office Action mailed Oct. 20, 2021 in U.S. Appl. No. 16/258,112, filed Jan. 25, 2019, 12 pages.
Rodriguez, Response filed Jan. 20, 2022, to USPTO Office Action mailed Oct. 20, 2021 in U.S. Appl. No. 16/258,112, 13 pages.
USPTO, Office Action mailed Apr. 25, 2022 in U.S. Appl. No. 16/258,112, filed Jan. 25, 2019, 18 pages.
Canadian IP Office, Office Action dated Jan. 27, 2020, in Canadian app. No. 3,029,678.
Rodriguez, Response filed May 14, 2020, to CIPO Office Action mailed Jan. 27, 2020 in Canadian app. No. 3,029,678.
Canadian IP Office, Office Action dated Dec. 6, 2021, in Canadian app. No. 3,029,678.
Rodriguez, Response filed Apr. 1, 2022, to CIPO Office Action mailed Dec. 6, 2021 in Canadian app. No. 3,029,678.
Canadian IP Office, Office Action dated Oct. 25, 2022, in Canadian app. No. 3,029,678.
Rodriguez, Response filed Feb. 22, 2023, to CIPO Office Action mailed Oct. 25, 2022 in Canadian app. No. 3,029,678.
Canadian IP Office, Office Action dated Dec. 8, 2023, in Canadian app. No. 3,029,678.
Rodriguez, Response filed Apr. 5, 2024, to CIPO Office Action mailed Dec. 8, 2023 in Canadian app. No. 3,029,678.

APPARATUS FOR MICROORGANISM ISOLATION, CHARACTERIZATION, AND IDENTIFICATION, AND METHODS OF USE

CROSS REFERENCE TO RELATED APPLICATIONS

This application is a continuation of U.S. patent application Ser. No. 17/895,616, filed Aug. 25, 2022, which was a divisional of parent U.S. patent application Ser. No. 16/258,112, filed Jan. 25, 2019. The parent application, and therefore the divisional application and the present application, claim the benefit of U.S. Provisional Application No. 62/622,493, filed Jan. 26, 2018. The disclosure of the divisional application, the parent application, and the provisional application are all incorporated by reference herein in their entireties.

BACKGROUND INFORMATION

Technical Field

The present disclosure relates generally to an apparatus and methods of using the same for microorganism growth, isolation, characterization and identification. In particular, the disclosed apparatus allows for controlled microbe growth and isolation based on oxygen, pressure, culture media gradients and metabolites. In each embodiment, the apparatus of the disclosure is particularly useful for the purpose of isolation of difficult to grow or never before cultured species of microorganisms and their by-products.

Background Art

It has been estimated that only 2% of all microbial isolates can be cultured in a lab. Therefore, the microbes that can be grown in the laboratory represent only a small fraction of the total diversity that exists in nature. At all levels of microbial phylogeny, uncultured clades that do not grow on standard media are playing critical roles in cycling carbon, nitrogen, and other elements, synthesizing novel by-products, and impacting the surrounding organisms and environment. While molecular techniques, such as metagenomic sequencing, can provide some information independent of the ability to culture these organisms, it is difficult to learn new gene and pathway functions from pure sequence data. Moreover, cultivation and expansion of these organisms remains challenging. A true understanding of the physiology of these bacteria and their roles in ecology, host health, and natural product production requires their cultivation in the laboratory.

The ability to culture difficult to culture or previously uncultured microbial strains provides a wealth of information about their role in the environment, ecology, and nutrient cycling. But perhaps even more importantly, screening of novel isolates will reveal novel products that can have profound effects for the discovery of novel drugs, improve agricultural techniques and products, promote and improve petroleum oil recovery, and identify novel biopolymers and biosurfactants.

Thus, there is a need for an apparatus and methods which allow for isolation, characterization and identification of microorganisms including previously difficult to culture or uncultured microorganisms in a sensitive, direct and efficient manner. Additionally, there is a need for novel methods of screening of novel isolates for the identification and isolation of novel by-products.

Other objects, advantages and features of the present disclosure will become apparent from the following specification taken in conjunction with the accompanying figures.

SUMMARY

It is an object of the present disclosure to provide an apparatus and method for isolating and culturing microorganisms including previously "unculturable" microorganisms.

The present disclosure provides an apparatus for the culture of microorganisms, wherein the apparatus generally comprises a body having an interior, an exterior, an upper end, an opening in the upper end configured to receive a sample, a closed lower end opposite of the upper end, a base attached to the lower end allowing the apparatus to stand upright and at least one lateral port opening attached to the body between the upper end and lower end, wherein the lateral port opening comprises an internal aperture adapted to allow access to the interior cavity of the apparatus and optionally comprise a removably attached cap. In preferred embodiments, a plurality of lateral port openings are attached to the body between the upper end and lower end.

The present disclosure further provides a library of microorganisms obtained using the apparatus as disclosed herein.

The present disclosure still further provides a method for screening and identification of new drugs and other substances of commercial interest in the pharmaceutical, chemical, biotechnology, and other industries as well as in the agriculture, which comprises cultivating a previously unculturable microorganism or screening a library of previously unculturable microorganisms, and isolating and identifying compounds having biological or other activity of interest.

The present disclosure still further provides microbial tablet formulations, wherein microorganisms are isolated from the apparatus as described herein.

While multiple embodiments are disclosed, still other embodiments of the present disclosure will become apparent to those skilled in the art from the following detailed description, which shows and describes illustrative embodiments of the disclosure. Accordingly, the figures and detailed description are to be regarded as illustrative in nature and not restrictive.

BRIEF DESCRIPTION OF THE DRAWINGS

FIG. 1 shows the body of the apparatus having a base comprising a circular cross-sectional shape; six lateral port openings oriented vertically to each other. The distal end of the lateral port opening (which extends away from the internal cavity of the apparatus) is threaded as a means to secure a cap. The upper end of the body of the apparatus has an opening configured to receive a sample and a closed lower with a base attached.

FIG. 2 shows the body of the apparatus having a base comprising a circular cross-sectional shape; six lateral port openings oriented vertically to each other. The distal end of the lateral port opening (which extends away from the internal cavity of the apparatus) is threaded as a means to secure a cap. The upper end of the body of the apparatus has an opening configured to receive a sample and a closed lower with a base attached. The lateral port opening closest to the upper end of the body shows the cap removed from the distal end showing the threading and internal aperture of the lateral port opening, as illustrated in FIG. 2. FIG. 2 also shows exemplary tablets which comprise microorganisms isolated from the apparatus.

DETAILED DESCRIPTION

The present disclosure relates to an apparatus and method of use thereof. The apparatus of the present disclosure has many advantages over traditional laboratory culturing techniques. For example, the disclosed apparatus allows for methods for isolation and culture of microorganisms from any environmental source. Thus, allows for the growth of previously unculturable organisms.

It is understood that the embodiments of this disclosure are not limited to a single apparatus, but the apparatus as disclosed herein can vary and is understood by skilled artisans. It is further to be understood that all terminology used herein is for the purpose of describing particular embodiments only, and is not intended to be limiting in any manner or scope. For example, as used in this specification and the appended claims, the singular forms “a,” “an” and “the” can include plural referents unless the content clearly indicates otherwise. Further, all units, prefixes, and symbols may be denoted in its SI accepted form.

Numeric ranges recited within the specification are inclusive of the numbers defining the range and include each integer within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾ This applies regardless of the breadth of the range.

Various aspects of the disclosure are described in further detail in the following sections.

I. Apparatus

Figure 2:
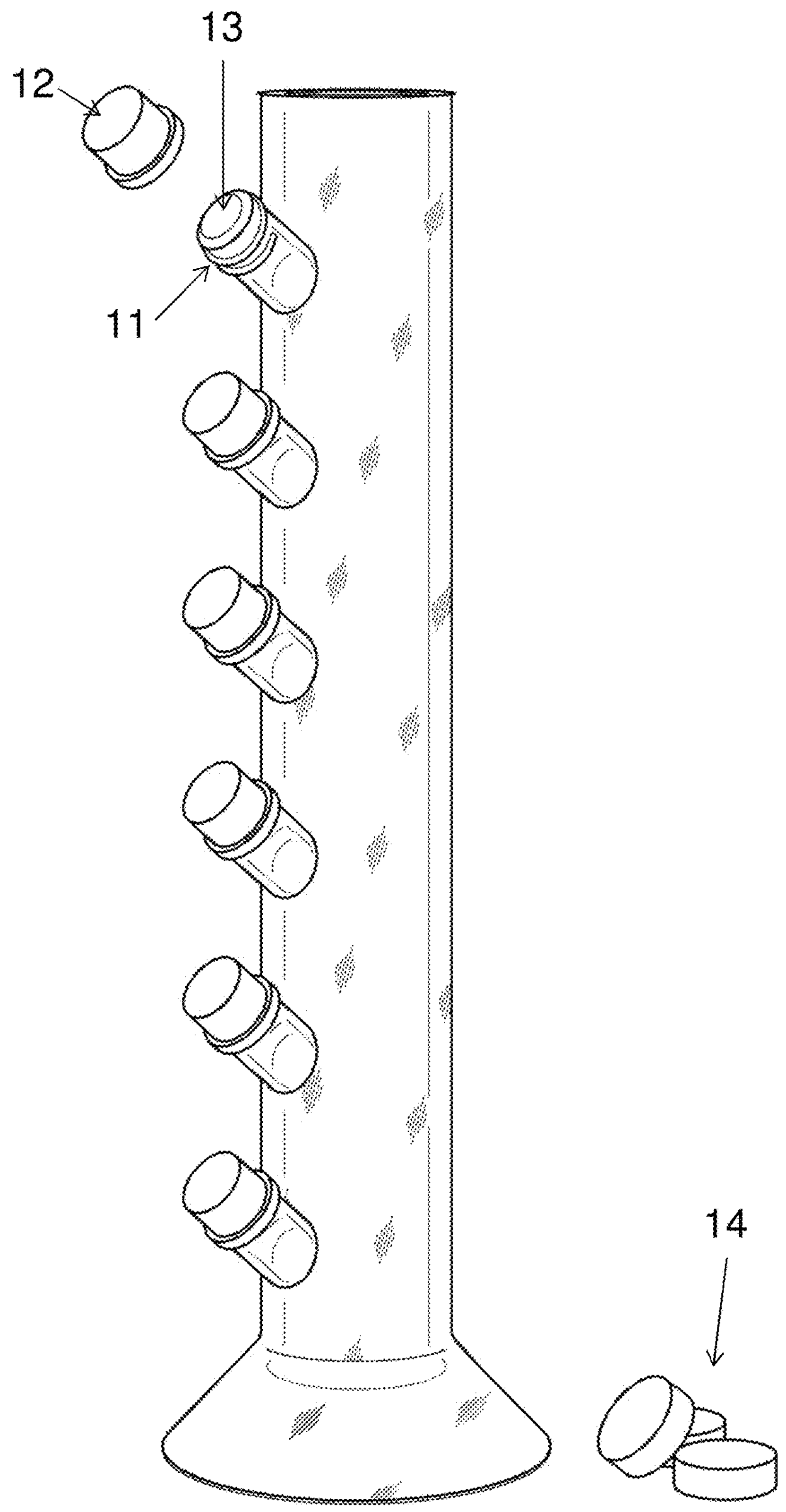
FIG. 2 is a schematic illustration of the apparatus in accordance with an exemplary embodiment.

An apparatus for carrying out the methods of the disclosure is designed to allow for the controlled growth, isolation and characterization of microorganisms including those that are difficult to culture or are uncultivable at the present time. This desired result can be achieved because the sample conditions within the apparatus can be adjusted, for example, to closely resemble that of the natural environment of the microorganisms. The lateral ports of the apparatus provide access to a sample retained in the interior cavity at different zones along the apparatus and to distinct gradients of the sample contained within the body of the apparatus affording the ability to precisely manipulate the exposure of the microorganisms to their environment (e.g. oxygen, nutrients, and pressure gradients). Thus, components of the environment, e.g., nutrients, growth factors, metabolites of other microbial species, etc., are easily controlled and optimized for growth and/or stimulation to microbial by-product formation. Furthermore, the by-products and organisms can be easily isolated through the specially placed lateral port openings without disturbing the other growth zones or gradients within the body of the apparatus In some embodiments, the apparatus 1 generally comprises a body 2 (e.g., an elongated cylinder) having an interior cavity 3, an exterior 4, an upper end 5, an opening in the upper end configured to receive a sample 6, a closed lower end opposite of the upper end 7, a base attached to the lower end 8, at least one sidewall between the upper end and lower end 9, wherein the at least one sidewall forms the interior cavity configured to retain the sample 3; and at least one lateral port opening attached to the at least one sidewall of the cylinder between the upper end and lower end 10, allowing access into the interior cavity 3 through the internal aperture 13 of the lateral port opening. In preferred embodiments, a plurality of lateral port openings are attached to the at least one sidewall between the upper end and lower end, allowing access to the interior cavity of the apparatus in a variety of positions between the upper and lower ends. The lateral port openings are adapted to allow access to the interior of the cylinder and can be opened and closed, in non-limiting examples by placing a cap, plug, gasket, septum and the like, on the distal end of the lateral port opening. FIG. 2 shows in some embodiments, the distal end of the lateral port opening are threaded 11 as a means to close the distal end with a cap 12.

(a) Body

Figure 1:
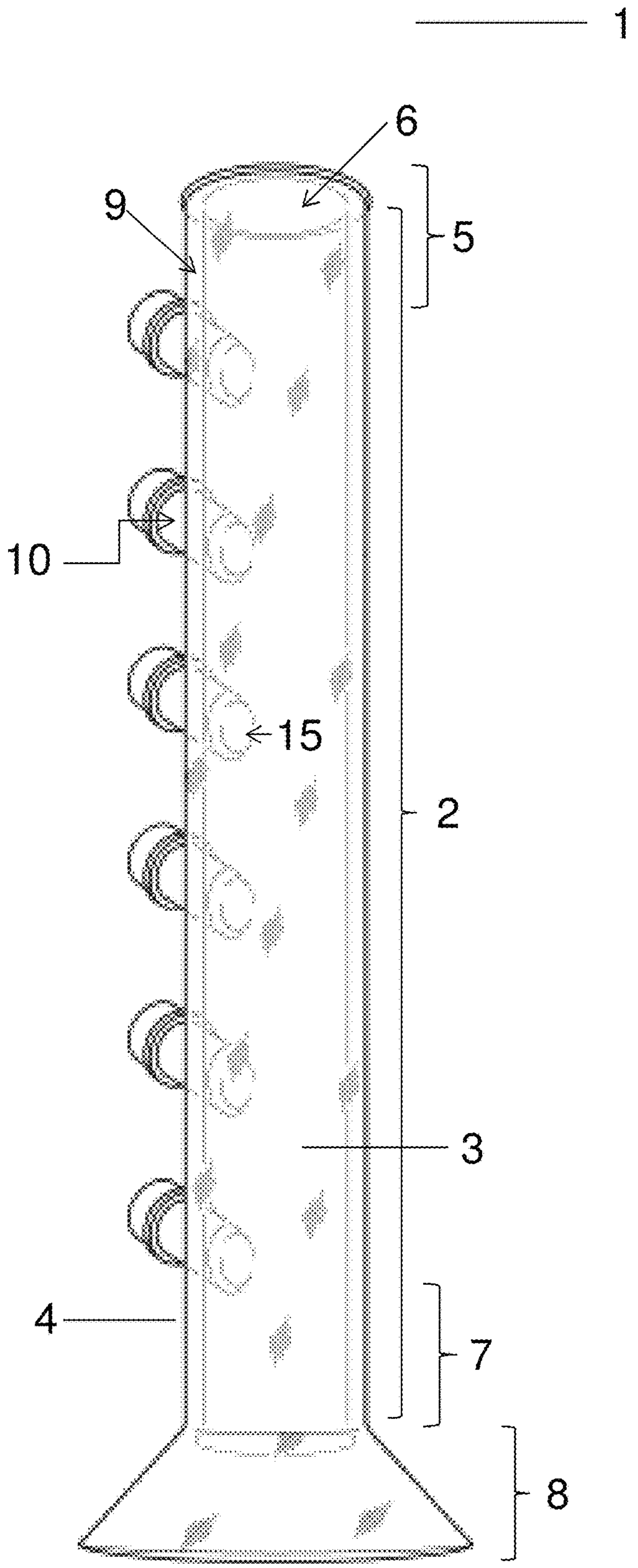
FIG. 1 is a schematic illustration of the apparatus in accordance with an exemplary embodiment.

FIG. 1 and FIG. 2 illustrate an exemplary embodiment of the apparatus for creating a culture environment for microorganisms, including microorganisms presently believed to be unculturable. The body of the apparatus has an interior cavity to retain a sample volume of a solid, liquid, or combination thereof. In non-limiting examples a sample may include one or more of, an environmental source (e.g., soil and/or water, suitable samples are discussed further in Section II), an appropriate nutrient medium, metabolites, microorganisms or combinations thereof. The opening in the upper end of the body is configured to receive the sample. The body of the apparatus may be any shape including, as a non-limiting example, an elongated cylinder. In a non-limiting example the body of the apparatus comprises a graduated cylinder for measuring the amount of sample provided to the interior cavity of the apparatus. In various embodiments, the interior cavity of the apparatus may hold various volumes, such as, but not limited to, 1 ml, 5 ml, 10 ml, 15 ml, 20 ml, 25 ml, 30 ml, 35 ml, 40 ml, 45 ml, 50 ml, 55 ml, 60 ml, 65 ml, 70 ml, 75 ml, 80 ml, 85 ml, 90 ml, 95 ml, 100 ml, 150 ml, 200 ml, 250 ml, 300 ml, 350 ml, 400 ml, 450 ml, 500 ml, 600 ml, 700 ml, 800 ml, 900 ml, 1000 ml, or greater. The body of the apparatus may be constructed of various types of materials such as, but not limited to, glass or plastic.

It is understood that the length and the diameter of the body of the apparatus may be configured to retain a desired amount of sample. In general, a smaller length or diameter of the body of the apparatus will hold a smaller amount of sample relative to an apparatus body with a larger length or diameter. It is understood that the body of the apparatus may have various lengths and diameters. The upper end of the body includes an opening to the interior cavity of the apparatus which is used for receiving a sample. The upper end of the body may be adapted to allow for closing of the upper opening. For example, in one aspect, the upper end may comprise threads as a means to close the upper opening with a cap. In some embodiments, the body may optionally include a lid which attached to the upper end of the body and covers the upper end opening. The lid preferably comprises a means to fasten the lid to the upper end of the cylinder. The lower end of the body may include an opening in an embodiment and may be closed in other embodiments.

The body preferably has a circular cross sectional shape forming a conventional elongated cylinder shape. However, the body may have various other types of cross sectional shapes such as, but not limited to, oval, square, rectangular, triangular, octagon, and the like. The body has at least one sidewall and may have a plurality of sidewalls. In an embodiment where the cross sectional shape is circular, the sidewall is represented by any lateral surface on the body of the apparatus which separates the exterior from the interior cavity. The sidewall of the apparatus is not limited to a particular width, as the width of the sidewall may be adjusted to allow support to the lateral ports or to insulate the sample contained in the apparatus.

In some embodiments, at least a portion of the body is preferably comprised of a transparent or semi-transparent material to allow for viewing of the sample provided to the interior of the apparatus and for exposure of light to the sample provided to the interior of the apparatus. It is preferable that a substantial portion of the cylinder is comprised of a transparent or semi-transparent material, however, it is possible that the body of the apparatus comprises a vertical strip which is transparent (or semi-transparent) with the remaining portions of the body being opaque. In some aspects the body of the apparatus is completely opaque.

In some embodiments, the body includes a plurality of line markings that are horizontally orientated to indicate a volume of sample in the cylinder at a certain location. The body may further include a plurality of measurement indicia corresponding to the plurality of line markings.

In some embodiments, the body comprises a closed lower end attached to a base allowing the apparatus to remain in an upright position. The base is attached to the lower end of the body and may have various cross sectional shapes such as, but not limited to, circular, oval, square, rectangular, triangular, octagonal and the like. The base may be non-removably attached to the lower end of the body or may be removably attached to the body of the apparatus. The base may be constructed of various types of materials such as, but not limited to, glass or plastic. In some embodiments, the base is made of the same material as the body.

(b) Lateral Port Opening

At least one lateral port opening is attached to the sidewall of the apparatus between the upper and lower ends of the body. Preferably, a plurality of lateral port openings are attached to at least one sidewall of the apparatus between the upper and lower ends of the body. The lateral port opening(s) allow for access to the sample within the interior cavity of the apparatus. In various aspects, the lateral port openings comprise a distal end and a proximal end. The proximal end is attached to the sidewall of the body of the apparatus such that no sample loss occurs at the point of connection. The lateral port opening may have any of cross sectional shapes such as, but not limited to, circular, oval, square, rectangular, triangular, octagonal, and the like. The lateral port opening has a hollow interior so as to provide access from the exterior of the apparatus, through an opening in the sidewall of the body of the apparatus at the point of connection with the lateral port, into the interior cavity. Said another way, the lateral port opening(s) comprise and internal aperture 13 which is continuous with hole in sidewall 15 at the point of connection with the lateral port, so as to allow access to the interior cavity of the body. In some embodiments, the lateral port opening is bent or curved as it extends away from the body of the apparatus. In other embodiments, the lateral port opening is does not bend or curve.

The lateral port openings may be attached to the body in an orientation that angles to the upper end of the body, angles to the lower end of the body or is perpendicular to the body.

It is understood that the length and the diameter of the lateral port opening may vary. In general, the length or diameters of the lateral port openings are relative to the length or diameter of the body of the apparatus. In some embodiments, the lateral port openings maintain the same diameter as they extend distal for the body of the apparatus. In some embodiments the lateral port openings have a smaller or larger diameter as they extend distal for the body of the apparatus.

In some embodiments, the lateral port openings are of the same material used for the body of the apparatus.

In the various embodiments, the plurality of lateral port openings are aligned about less than on inch from each other, about 1 inch from each other or greater than one inch from each other. Preferably the lateral port openings are attached to the cylinder and are 2 inches apart from each other. The plurality of lateral port openings may be aligned in a vertical orientation relative to each other or may be off-set in the vertical axis from each other. In some embodiments, the lateral port opening(s) are configured as a means to cover or close the internal aperture. In some embodiments, the lateral port openings are threaded on the distal end as a means to fasten a cap to each opening thereby closing off the internal aperture of the lateral port. In some embodiments, the distal end of the lateral port opening(s) may comprise one or more of a filter, a gasket, a septum, a plug or the like. In some embodiments, the lateral port openings are configured for syringe insertion in the internal aperture of the lateral port into the interior of the apparatus to capture microorganisms in their natural media allowing for transfer of the microbes into both aerobic and anaerobic tubes for further analysis.

Generally speaking the number of lateral port openings attached to at least one sidewall can be any number of openings that can be reasonably attached to the body. The number of lateral port openings of the apparatus can be about 2 or more, about 3 or more, about 4 or more, about 5 or more, about 6 or more, about 7 or more, about 8 or more, about 9 or more, about 10 or more, about 11 or more, about 12 or more, about 13 or more, about 14 or more, about 15 or more, about 16 or more, about 17 or more, about 18 or more, about 19 or more, about 20 or more, about 21 or more, about 22 or more, about 23 or more, about 24 or more or about 25 or more. Additionally, the number of lateral port openings of the apparatus can be about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24 or about 25. Further, the number of lateral port openings of the apparatus can be 2 or more, 3 or more, 4 or more, 5 or more, 6 or more, 7 or more, 8 or more, 9 or more, 10 or more, 11 or more, 12 or more, 13 or more, or 14 or more, 15 or more, 16 or more, 17 or more, 18 or more, 19 or more, 20 or more, 21 or more, 22 or more, 23 or more, 24 or more or 25 or more. Still further, the number of lateral port openings of the apparatus can be 1, 2, 3, 4, 5, 6, 7, 8, 9, 10, 11, 12, 13, 14, 15, 16, 17, 18, 19, 20, 21, 22, 23, 24, or 25.

II. Methods of Use

The methods of the present disclosure allow growth and isolation/identification of new types of microorganisms, such as bacteria, previously considered as "unculturable", and the establishment of libraries of uncultivable microorganisms. In some embodiments, the microbe isolated for the apparatus disclosed herein are formulated in a tablet optionally comprising suitable nutrients for the microbes. A suitable apparatus for the method of the invention are those described in Section I.

In one embodiment, the present disclosure relates to a method for isolation, culture or expansion of microorganisms, including microorganisms from any environmental source (e.g. previously unculturable microorganisms), which comprises: (i) collecting a sample from an environmental source; (ii) diluting the sample in an appropriate medium; (iii) incubating the sample within the interior of an apparatus disclosed herein for an appropriate time; and (iv) isolating the microorganism(s) from one or more of the plurality of the lateral ports of the apparatus. In some embodiments, step (iv) may be repeated multiple times throughout the incubation period.

The sample can be any sample that includes a microorganism. In non-limiting examples, the sample is an environmental sample are collected from any terrestrial, aquatic or marine source such as soil, biofilms, sediments (e.g. coral or other marine sediments, aquifer sediments and the like), waste waters, sludge residue, crude oil (e.g., API 14). In some embodiments, the sample may be collected from a food (e.g., raw materials, in-process samples, and finished-product samples), a beverage, a clinical or veterinary sample (e.g., blood, serum, plasma, urine, sputum, tissue, mucous, feces, wound exudate, pus, cerebrospinal fluid) and the like. The sample can be suspended in its natural medium or diluted in another appropriate medium. The sample may be divided, for example, into 1-ml tubes, and each divisional sample may then subjected to counting/estimation of the number of microorganisms by well-known techniques, for example by DAPI (4',6-diamidino-2-phenylindole) staining of the cells and direct microscopic count of the DAPI-stained cells.

The samples may be diluted as necessary, in an appropriate medium. As used herein, an "appropriate medium" is intended to mean a medium compatible with the environment from which the sample has been collected with respect to physico-chemical parameters such as pH, salinity, temperature, oxygen concentration, and the like. In non-limiting examples, the medium may be sterile water, sterile saline, sterile water containing suitable ingredients for compatibility with the environmental source, glucose enriched MOPS (3-(N-Morpholino) Propane-Sulfonic Acid) broth, enriched Nutrient broth or Tryptic Soy broth, and the like. Additionally, the appropriate medium may also be supplemented with additional vitamins, minerals, amino acids, polypeptides, nucleic acids, small molecules and the like. For example, when the sample is collected from soil, the medium may be sterile water. When the sample collected from a marine source, for example, the medium will have the salinity corresponding to the marine source and the salt concentration will be higher if the sample is originated from the Dead Sea.

In one aspect, the medium may be mixed with a gelating agent as a matrix to the samples. Any suitable natural, semi-synthetic or synthetic gelating agent may be used such as, but not limited to, agar, alginate, carrageenans, gum Arabic, guar gum, traganth gum, xanthan gum, propyleneglycolalginate, and mycrocrystalline cellulose.

The next step consists of the incubation of the sample containing one or more microorganisms optionally in the environment from which the original sample has been collected, for an appropriate time. This is the alternative to cultivate such microorganisms that cannot grow in known growth media for microorganisms. The incubation in the environment can take from days to months. In one embodiment, the sample is incubated for at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, at least 30 days, at least 31 days, at least 1 month, at least 2 months, at least 3 months, at least 4 months, at least 5 months, at least 6 months or longer. The sample may be incubated in a controlled environment (e.g. in an incubator) or in an ambient environment. The sample may be incubated at an appropriate temperature which supports the growth of the microorganism. Temperature of the sample may be controlled by any known means including using, in non-limiting examples, a temperature mat or incubator. The sample can be incubated in direct sunlight, indirect sunlight, in darkness or any combination thereof. Additional, light may be provided by an artificial source at any suitable wavelength and/or intensity. $O_2$ and $CO_2$ levels may be monitored and adjusted accordingly to support growth of the microorganisms or the formation by by-products. Furthermore, the addition of final electron acceptors and/or final electron donors and/or hydrogen donors may be monitored and modulated using methods know to the skilled artisan.

Throughout the incubation period of the sample within the apparatus, microorganisms may be isolated at each gradient zone of the sample concurrent with the nearest lateral port opening in a manner which minimizes the disturbance of the sample. For example, isolating a microorganism or by-product may occur by inserting a sterile instrument through the aperture and/or septum of lateral port opening of the apparatus into the specific gradient of the sample contained therein. Any suitable sterile instrument may be used (e.g. syringe or tooth pick). Preferably, all steps in the methods described herein are completed using aseptic technique. Optionally, the isolated microorganisms are transferred from the sample into both aerobic and anaerobic containers holding pre-prepared and sterilized indigenous culture media as a culture base.

In one embodiment of the disclosure, cells or extracts from microorganisms are subjected to analysis by 16S RNA gene sequencing. Ribosomal RNA genes from the samples, microcolonies or cultures are amplified by PCR by using specific 16S RNA oligonucleotide primers for bacteria. After cloning the PCR products, the inserts are screened by their restriction patterns (RFLP—restriction fragment length polymorphism). The clones are submitted to sequence analysis and compared with known 16S RNA genes using, for example, the online GenBank database (http://ncbi.nlm-.nih.gov/GenBank). In this way, it can be determined whether or not the microorganism represents a new species/genus.

The present disclosure further provides a method for genomic characterization of microorganisms, which comprises: (i) collecting a sample from an environmental source;

(ii) diluting the sample in an appropriate medium; (iii) incubating the sample within the apparatus disclosed herein for an appropriate time; (iv) isolating the microorganism(s) from one or more of the plurality of the lateral ports of the apparatus; (vi) extracting the microorganisms by chemical lysis using an agent for extraction of genomic DNA; (v) processing the total genomic DNA to establish the restriction fragment length polymorphism (RFLP) pattern of the microorganisms; (vi) analyzing the RFLP patterns to identify unique clones that are submitted to sequence analysis; and (vii) identifying the microorganisms by comparison of these sequences with sequences available at the GenBank database.

In one preferred embodiment, a method is provided wherein the microorganisms are isolated from an agricultural environmental source, which comprises: (i) collecting a sample from an environmental source; (ii) diluting the sample in an appropriate medium; (iii) incubating the sample within the apparatus of the disclosure for an appropriate time; (iv) isolating the microorganism(s) from one or more of the plurality of the lateral ports of the apparatus; (vi) extracting the microorganisms by chemical lysis using an agent for extraction of genomic DNA; (v) processing the total genomic DNA to establish the restriction fragment length polymorphism (RFLP) pattern of the microorganisms; (vi) analyzing the RFLP patterns to identify unique clones that are submitted to sequence analysis; and (vii) identifying the microorganisms by comparison of these sequences with sequences available at the GenBank database.

In a further aspect, the present disclosure relates to a library of previously uncultured microorganisms obtained by using the apparatus as disclosed herein and to the use of said library for the discovery of new biologically active agents including, but not limited, to new antibiotics, enzymes, biopolymers, biosurfactants, biocatalysts, and/or genes.

In a further aspect, the present disclosure relates to new products, which include but are not limited to, antibiotics, enzymes, biopolymers, biosurfactants, biocatalysts, and/or genes expressed or produced by the microorganisms which are isolated or cultured using an apparatus disclosed herein. Beyond the intrinsic interest of discovering new microbial species, the methods of the disclosure have the potential to provide an important source of diverse organisms for the development and production of novel compounds, e.g., small molecules, enzymes and antibiotics, for pharmaceutical, agricultural, chemical and industrial markets. The methods described herein can be used, e.g., for the discovery of products with activity against diseases and conditions that afflict mammals, such as cancer, immunodeficiency virus infection, microbial infections (e.g., bacterial and fungal infections), lipid metabolism disorders, inflammation, diabetes and the like. Such natural products discovered according to the present method can serve as lead compounds in drug discovery programs. Such drug discovery programs predicated on the novel natural products obtained via the apparatus as disclosed herein and can employ the logic and methods of classical medicinal chemistry, computer-aided "rational" drug design, combinatorial or parallel synthesis protocols, combinatorial or parallel assay protocols, or any possible amalgamation of these methods and approaches. Novel products identified from using the apparatus as disclosed herein, or compounds resulting from drug discovery programs based on the use of the apparatus as disclosed herein, as lead compounds, may be formulated and used as pharmaceutical, agricultural or veterinary agents.

After incubation in the apparatus of the disclosure, microorganisms can be isolated and then subjected to molecular biology and genomics techniques, and/or cultured for the production of bioactive materials. Libraries can be construed composed of microorganisms; each isolated from a separate region within the apparatus, and can be used for identification of new biologically active compounds, even without identification and characterization of the microorganisms. When the identified biologically active compound is a small organic molecule, its structure can be determined by known methods, it is then synthesized, the biological activity is ascertained and it can then be formulated in pharmaceutical or veterinary compositions. The method enables exploration of new products from previously uncultured microorganisms. New genes might be obtained from the previously uncultivable microbial communities, and new biologically active materials such as proteins, enzymes and antibiotics of utility to humans may be discovered.

The ability to detect the presence of novel products is central to the practice of the subject disclosure. In general, assays, especially high throughput assays, are carried out to detect organic molecules and the like that are produced as part of a de novo synthesis pathway using an apparatus as disclosed herein. For example, a candidate microorganism cultured and isolated from an apparatus as described herein is first screened for bioactivity. As used herein, "bioactivity" refers to the ability of a biomolecular composition to confer a desired property during and/or after contact of said biomolecular composition for a condition normally assayed for in a standard assay procedure for a material formulation. In non-limiting examples, such normally assayed conditions include whole cells or biomolecules of a specific microorganism screened for antimicrobial activity, improved crop health or yield, pest control, improved oil recovery of petroleum hydrocarbons, improved environmental salinity remediation, improved and accelerated chemical remediation, increased pesticide residue degradation and enzymatic activity. Then, the compound or gene responsible for the observed bioactivity can be isolated and analyzed further.

According to the disclosure, metagenomics techniques can be used to address the genetic structure and functional composition of a sample irrespective of whether the microorganism can be cultured. Molecular methodologies such as PCR of select molecular targets can be used to discover genes with useful properties. Microbial communities can be profiled by techniques well known in the art. Cloning and sequencing of molecular targets such as 16S rDNA enable identification of indigenous and novel organisms.

It is further envisaged to construct bacterial artificial chromosome [BAC], cosmid and small insert libraries from diverse environmental samples and then subject the libraries to a screening for novel genes, proteins and small molecules exhibiting activities of interest. For example, 16S rRNA gene clone libraries can be formed from mixed colonies of microorganisms and screened.

As noted above, the colonies of microorganisms can also be screened for antibiotic activity by contacting diluted samples with a strain of interest and studying the influence on its growth. Colonies of unculturable microorganisms that produce compounds with antibiotic activity will inhibit growth of strains. Said compounds can then be isolated, purified, analyzed and either synthesized for use as antibiotic or used as a model for further drug discovery. In an exemplary embodiment, whole cells of a specific microorganism can be screened for antimicrobial activity using the apparatus as described above. For example, an environmental sample containing microbial cells is diluted so that the sample contains preferably 1-100 cultivable cells. This sample is mixed medium containing a test strain, e.g., *B. subtilis*, at a concentration of, e.g., $10^6$ cells/ml, the test sample is then placed in the apparatus of the disclosure. The test sample is incubated to allow uncultivated cells to replicate. Empty zones of no or little *B. subtilis* growth are present around colonies of uncultivables that produce antibiotics are an induction of antimicrobial activity. Therefore, colonies of uncultivable organisms that produce antimicrobials will inhibit growth of test strains, producing empty zones or regions within the apparatus.

Libraries of test extracts of the microorganisms can also be tested for activity by automated high throughput biochemical, enzymatic or biological assays using, for example, a panel of test microorganisms to test antibiotic activity, or a panel of enzymes or antibodies to find compounds that affect their activities. The high throughput processing and analysis of large libraries of test extracts or compounds may be automated, e.g., using automated/robotic systems. This automation can include, for instance, such activities as: 1) arraying and storage of libraries of extracts or compounds; and 2) screening subject extracts and compounds in biological and biochemical assays. The details of the specific methods utilized will vary from one embodiment to the next, but can be readily implemented by those skilled in the art.

For example, for high throughput assays, the subject extracts or compounds may be tested for activity in high throughput biochemical or biological assays adapted for automatic readouts. For instance, extracts may be screened for antimicrobial activity by using a panel of test organisms to be read for, e.g., optical density. The goal is to develop an automated method that is sensitive and rapid. In addition to affinity assays, the test extracts or compounds can be tested in biochemical assays, such as competitive binding assays or enzyme activity assays. To increase throughput, it may be desirable to test pools of extracts from more than one novel organism in certain instances.

Novel bioactive compounds from organisms isolated or cultured in the apparatus as disclosed herein may be provided as pharmaceutically acceptable compositions, which comprise a therapeutically effective amount of one or more of the compounds described above, formulated together with one or more pharmaceutically acceptable carriers. Such pharmaceutical compositions may be used for testing or therapeutic purposes. The pharmaceutical compositions may be specially formulated for administration in solid or liquid form, suitable for, e.g., oral administration; parenteral administration, for example by subcutaneous, intramuscular or intravenous injection; topical application, for example, as a cream, ointment or spray applied to the skin; or intravaginally or intrarectally, for example, as a pessary, cream or foam.

The phrase "therapeutically effective compound" as used herein means that amount of a compound, material, or composition isolated using the apparatus disclosed herein, which is effective for producing some desired therapeutic effect.

The phrase "pharmaceutically acceptable carrier" as used herein means a pharmaceutically acceptable material, composition or vehicle involved in carrying or transporting the subject agent from one organ or portion of the body, to another organ or portion of the body without negative effect.

Formulations of pharmaceutical compositions described herein may conveniently be presented in unit dosage form and may be prepared by conventional methods well known in the art of pharmacy. The amount of active ingredient that can be combined with a carrier material to produce a single dosage form will vary depending upon the host being treated and the particular mode of administration.

Actual dosage levels of the active ingredients in the pharmaceutical compositions described herein may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound (or derivative) employed, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required.

In some embodiments, microorganisms cultured and isolated using an apparatus disclosed herein may be further formulated into a composition in the form of a granulate or soluble tablet 14 containing dried, viable, active microorganisms. The tablet formulation comprises a stabilizing agent which facilitates the manufacture of tablets that contain the active microorganisms, by direct compression of the formulation into tablets. The granulate or tablet formulations may optionally comprise suitable nutrients, vitamins, and the like. Suitable methods of generating such formulations are those known in the art, in non-limiting examples such as disclosed in WO2010109436 A1 published Sep. 30, 2010, WO2005060937 A1 published Jul. 7, 2005, and WO2017069717 A1 published Apr. 27, 2017, the disclosures of which are herein incorporated by reference.

Definitions

So that the present disclosure may be more readily understood, certain terms are first defined. Unless defined otherwise, all technical and scientific terms used herein have the same meaning as commonly understood by one of ordinary skill in the art to which embodiments of the disclosure pertain. Many methods and materials similar, modified, or equivalent to those described herein can be used in the practice of the embodiments of the present disclosure without undue experimentation, the preferred materials and methods are described herein. In describing and claiming the embodiments of the present disclosure, the following terminology will be used in accordance with the definitions set out below.

The term "about," as used herein, refers to variation in the numerical quantity that can occur, for example, through typical measuring techniques and equipment, with respect to any quantifiable variable, including, but not limited to, mass, volume, time, distance, wave length, frequency, voltage, current, and electromagnetic field. Further, given solid and liquid handling procedures used in the real world, there is certain inadvertent error and variation that is likely through differences in the manufacture, source, or purity of the ingredients used to make the compositions or carry out the methods and the like. The term "about" also encompasses amounts that differ due to different equilibrium conditions for a composition resulting from a particular initial mixture. The term "about" also encompasses these variations. Whether or not modified by the term "about," the claims include equivalents to the quantities.

The apparatus and methods of the present disclosure may comprise, consist essentially of, or consist of the components and steps of the present disclosure as well as other ingredients or steps as described herein. As used herein, "consisting essentially of" means that the methods, systems, apparatuses and compositions may include additional steps, components or ingredients, but only if the additional steps, components or ingredients do not materially alter the basic and novel characteristics of the claimed methods, systems, apparatuses, and compositions.

The term "surfactant" refers to a molecule having surface activity, including wetting agents, dispersants, emulsifiers, detergents, and foaming agents, and the like. It is understood to be inclusive of the use of a single surfactant or multiple surfactants.

The term "weight percent," "wt. %," "wt-%," "percent by weight," "% by weight," and variations thereof, as used herein, refer to the concentration of a substance as the weight of that substance divided by the total weight of the composition and multiplied by 100.

As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Use of Apparatus to Culture Indigenous Microorganisms from Agriculture Soil Agriculture soil from a Texas farm was weighed and measured to 200 grams on a scale. The soil was then aseptically added to the culture apparatus where it fell to the base of the apparatus.

Farm irrigation water along with a 15% diluted nutrient base taken from either an enriched Nutrient broth or Tryptic Soy broth was then poured over the soil to the top demarcated line.

All port caps were closed and secured tightly prior to agitation of the soil and water medium, resulting in a homogenous mix.

The apparatus was placed for incubation by a window for indirect sunlight to allow for photosynthetic organisms to be selected at their preferred oxygen gradient range within the culture vessel apparatus. Additionally, a temperature mat was placed beneath the apparatus to regulate temperature within the vessel.

The incubation period was approximately 24-28 days to allow for cultivation of fastidious organisms within the culture gradient zones.

Throughout the incubation period the culture apparatus was regularly checked for microorganism presence at each gradient zone within the chamber in a manner to minimize disturbance. This occurs via inserting a sterile syringe into the specific gradient port opening through the aperture and septum and transferring the sample into both aerobic and anaerobic glass tubes holding pre-prepared and sterilized indigenous culture media as a culture base.

Further microbial, biochemical, enzymatic and morphological analysis a full characterization of the unique microbes can be obtained, classified, stored and continually sub-cultured. The discovery of novel varieties of *Streptomyces, Pseudomonas, Bacillus* and *Clostridium* may lead to new protein by products for agricultural soil health and pest biocontrol.

Example 2—Use of Apparatus to Culture Indigenous Microorganisms from Heavy Crude Oil Heavy crude oil (API 14) from a Texas lease oil well was weighed and measured to 200 grams on a scale. The heavy crude oil was then aseptically added to the culture apparatus where it fell to the base of the apparatus.

Produced well water along with a 15% diluted nutrient base taken from either an enriched Nutrient broth or Tryptic Soy broth was then poured over the soil to the top demarcated line.

All port caps were closed and secured tightly for slight agitation of the crude oil and water medium.

The apparatus was placed for incubation by a window for indirect sunlight to allow for photosynthetic organisms to be selected at their preferred oxygen gradient range within the culture vessel apparatus. Additionally, a temperature mat was placed beneath the apparatus to regulate temperature within the vessel.

The cultivation period was approximately 24-28 days to allow for cultivation of fastidious organisms within the culture gradient zones.

Throughout the cultivation period the culture apparatus was regularly checked for microorganism presence at each gradient zone within the chamber in a manner to minimize disturbance. This occurs via inserting a sterile syringe into the specific gradient port opening through the aperture and septum and transferring the sample into both aerobic and anaerobic glass tubes holding pre-prepared and sterilized indigenous culture media as a culture base.

Through further microbial, biochemical, enzymatic and morphological analysis a full characterization of the unique microbes can be obtained, classified, stored and continually sub-cultured.

The selection of facultatively anaerobic microorganisms capable of expressing novel enzymes for the degradation or metabolism of hydrocarbons found within oil saturates, aromatics, resinoids and asphaltenes are essential to promote and improve petroleum oil recovery in the reservoir formation worldwide.

Example 3—Use of Apparatus to Culture Microorganisms, Preferably *Pseudomonas* Species for Novel Biopolymer and Biosurfactant Expression Sludge residue from a waste processing facility was weighed and measured to 200 grams on a scale. The sludge residue was then aseptically added to the culture apparatus where it fell to the base of the apparatus.

Residual sludge water along with a *Pseudomonas* enriched media for *Pseudomonas* selection was blended together. This consisted of 15% diluted nutrient base taken from a glucose enriched MOPS broth supplemented with King A for increased pyocyanin production was then poured over the residue sludge to the top demarcated line.

The apparatus was placed for incubation by a window for indirect sunlight to allow for photosynthetic organisms to be selected at their preferred oxygen gradient range within the culture vessel apparatus. Additionally, a temperature mat was placed beneath the apparatus to regulate temperature within the vessel.

The cultivation period was approximately 24-28 days to allow for cultivation of fastidious organisms within the culture gradient zones.

Throughout the cultivation period the culture apparatus was regularly checked for microorganism presence at each gradient zone within the chamber in a manner to minimize disturbance. This occurs via inserting a sterile syringe into the specific gradient port opening through the aperture and septum and transferring the sample into both aerobic and anaerobic glass tubes holding pre-prepared and sterilized indigenous culture media as a culture base.

Through a high number of microbial, biochemical, enzymatic and morphological microscopic analysis an expansive characterization of the unique microbes can be obtained, classified, stored and continually sub-cultured for further study.

The selection of facultatively anaerobic microorganisms capable of expressing novel enzymes, biopolymers and biosurfactants for the use in a variety of industries is essential and needed to improve surface interactions in a novel biological process.

Example 4—Use of the Apparatus of the Disclosure for Culture of Microorganisms and Novel Antibiotic Identification Agriculture soil from a disease infected crop field (Pythium and Bacterial Blight) was weighed and measured to 200 grams on a scale. The infected soil was then aseptically added to the culture apparatus where it fell to the base of the apparatus.

Irrigation water along with a 15% diluted nutrient base taken from a glucose enriched Nutrient broth was then poured over the infected soil to the top demarcated line.

All port caps were closed and secured tightly for slight agitation of the infected soil and water medium.

The apparatus was placed for incubation near by a window to allow for photosynthetic organisms to be selected at its preferred oxygen gradient range within the culture vessel apparatus.

The cultivation period was approximately 21-28 days to allow for growth of fastidious and other slow metabolizing organisms within the culture gradient zones.

Throughout the cultivation period the culture apparatus was regularly checked for microorganism presence at each gradient zone within the chamber in a manner to minimize disturbance. This occurs via inserting a sterile syringe into the specific gradient port opening through the aperture and septum and transferring the sample into both aerobic and anaerobic glass tubes holding pre-prepared and sterilized indigenous culture media as a culture base.

Additionally, minimum inhibitory assays (MIC) were conducted to challenge the expression of antibiotics from the newly discovered microbes against common fungal and bacterial disease organisms from agriculture fields. The presence and expression of strong and novel antibiotic and antimicrobial byproducts were seen from a number of newly isolated microorganisms.

Through a high number of microbial, biochemical, enzymatic and morphological microscopic analysis an expansive characterization of the unique microbes can be obtained, classified, stored and continually sub-cultured for further study.

The selection of microorganisms capable of expressing novel antibiotics, biofilms and enzymes via unique metabolic and expression processes for the use in combating disease in both agriculture and health care is essential for crop and animal health.

Example 5—Isolation and Identification of Soil Fertility Microorganisms from a Soil Sample Protocol Fertilizer macro/micro nutrient microorganisms were isolated from agriculture soils homogenously blended for microbial extraction. After adding approximately 400 grams of soil to the base of the apparatus, water was filled to 1 inch above the top port and allowed to sit and incubate for 3 days to allow for microbial zone gradation throughout the device. The substrates listed in table 1 were added at 5%/wt. to nutrient agar plates after which 1 ml of solution was extracted from each port via a sterile syringe. Then 0.1 ml was transferred to the enriched NA plates using a serial dilution protocol to allow for the isolation of single cell cultures for further characterization. These plates were allowed to incubate at incubation temperature ranges from 20° C.-50° C.

Once single colonies were isolated then further biochemical and enzymatic screening was conducted using classical microbiological and biochemical screening tests through BIOLOG micro plates and enzyme illumination techniques.

As a result, individual types and categories of microorganisms capable of solubilizing both specific macronutrients and micronutrients were determined and isolated for further characterization, development and commercialization.

TABLE 1

Isolation and identification of soil fertility microorganisms from a soil sample

| Element | Element | Substrate for Microbe Extraction | Isolation Port for Continued Protocol |
|---|---|---|---|
| N | Nitrogen | Ammonium Nitrate 30% | Isolated from Port 5 |
| P | Phosphorus | Potassium Phosphate 50% | Isolated from Port 4 |
| K | Potassium | Potassium Nitrate 50% | Isolated from Port 6 |
| B | Boron | Boron concentrate 80% | Isolated from Port 2 |
| Ca | Calcium | Calcium powder 60% | Isolated from Port 2 |
| Cu | Copper | Copper Magnesium 70% | Isolated from Port 3 |
| Mg | Magnesium | Magnesium concentrate 60% | Isolated from Port 3 |
| Mn | Manganese | Manganese Concentrate 70% | Isolated from Port 4 |
| Mo | Molybdenum | Molybdenum 90% | Isolated from Port 5 |
| S | Sulfur | Sulfur 80% | Isolated from Port 5 |
| Si | Silicone | Silicone 70% | Isolated from Port 4 |
| Zn | Zinc | Zinc Sulfate 80% | Isolated from Port 4 |

Method: BAM Ch 14 (Modified Protocol)
Method: AOAC 990.12
Method: Selective and Differential Media for Specific Strain Isolation

What is claimed is:

1. An apparatus for isolating and culturing microorganisms consisting essentially of:

a body having the shape of an elongated cylinder consisting essentially of: an upper end comprising an opening configured to receiving a sample;

a closed lower end opposite the upper end attached to a base allowing the apparatus to remain in an upright position;

at least one sidewall between the upper end and lower end, wherein the at least one sidewall forms an interior cavity; and three or more lateral port openings attached to the at least one sidewall of the elongated cylinder between the upper end and the closed lower end, each of the three or more lateral port openings:

having an aperture allowing access to the interior cavity, do not extend into a center of the interior cavity, having a distal end and a proximate end, each of the proximate ends attached to the at least one sidewall, are oriented vertically relative to each other on a same vertical axis on a same side of the elongated cylinder such that a microorganism sample can be isolated through one of the three or more lateral port openings without disturbing another microorganism sample taken from an adjacent one of the three or more lateral port openings.

2. The apparatus of claim 1, wherein the three or more lateral port openings comprises at least four lateral port openings.

3. The apparatus of claim 1, wherein the body is comprised of a transparent or semi-transparent material.

4. The apparatus of claim 1, wherein the body includes a plurality of line markings and a plurality of measurement indicia corresponding to the plurality of line markings.

5. The apparatus of claim 1, wherein each of the three or more lateral port openings comprise a removably attached cap to close each of the apertures.

6. The apparatus of claim 5, wherein at least one of the three or more lateral port openings comprises one or more of a filter, a gasket, and/or a septum.

7. The apparatus of claim 1, wherein the three or more lateral port openings are spaced vertically about 2 inches apart.

8. The apparatus of claim 1, wherein interior cavity holds sample volumes of about 5 ml, about 10 ml, about 15 ml, about 20 ml, about 25 ml, about 30 ml, about 35 ml, about 40 ml, about 45 ml, about 50 ml, about 55 ml, about 60 ml, about 65 ml, about 70 ml, about 75 ml, about 80 ml, about 85 ml, about 90 ml, about 95 ml, about 100 ml, about 150 ml, about 200 ml, about 250 ml, about 300 ml, about 350 ml, about 400 ml, about 450 ml, about 500 ml, about 600 ml, about 700 ml, about 800 ml, about 900 ml, about 1000 ml, or greater.

9. The apparatus of claim 1, wherein the body is constructed of glass or plastic.

* * * * *